(12) United States Patent
Nishizawa et al.

(10) Patent No.: US 12,239,527 B2
(45) Date of Patent: Mar. 4, 2025

(54) METHOD OF ABSORBING OR DISCHARGING WATER OF OPHTHALMIC MEDICAL DEVICE AND OPHTHALMIC MEDICAL DEVICE

(71) Applicant: TOHOKU UNIVERSITY, Sendai (JP)

(72) Inventors: Matsuhiko Nishizawa, Sendai (JP); Shotaro Yoshida, Sendai (JP); Shinya Kusama, Sendai (JP)

(73) Assignee: TOHOKU UNIVERSITY, Miyagi (JP)

( * ) Notice: Subject to any disclaimer, the term of this patent is extended or adjusted under 35 U.S.C. 154(b) by 849 days.

(21) Appl. No.: 17/310,995

(22) PCT Filed: Mar. 4, 2019

(86) PCT No.: PCT/JP2019/008475
§ 371 (c)(1),
(2) Date: Sep. 3, 2021

(87) PCT Pub. No.: WO2020/178964
PCT Pub. Date: Sep. 10, 2020

(65) Prior Publication Data
US 2022/0117724 A1    Apr. 21, 2022

(51) Int. Cl.
*A61F 2/16* (2006.01)
*A61F 9/00* (2006.01)
(Continued)

(52) U.S. Cl.
CPC .............. *A61F 2/16* (2013.01); *A61F 9/0017* (2013.01); *A61F 9/007* (2013.01); *G02C 7/04* (2013.01); *A61N 1/325* (2013.01)

(58) Field of Classification Search
CPC ... A61F 9/00781; A61F 9/0017; A61N 1/325; A61N 1/36046; A61K 9/0009; A61K 9/0051
See application file for complete search history.

(56) References Cited

U.S. PATENT DOCUMENTS

| | | | |
|---|---|---|---|
| 2016/0213514 A1* | 7/2016 | Manzo | A61N 1/30 |
| 2017/0258635 A1* | 9/2017 | Reynard | A61N 1/205 |
| 2018/0217402 A1 | 8/2018 | Larmagnac et al. | |

FOREIGN PATENT DOCUMENTS

| | | |
|---|---|---|
| CN | 103197437 A | 7/2013 |
| JP | 2016067401 A | 5/2016 |

(Continued)

OTHER PUBLICATIONS

Mar. 28, 2023, Notification of Reasons for Refusal issued by the Japan Patent Office in the corresponding Japanese Patent Application No. 2021-503300.
(Continued)

*Primary Examiner* — Andrew J Mensh
*Assistant Examiner* — Meagan Ngo
(74) *Attorney, Agent, or Firm* — KENJA IP LAW PC

(57) ABSTRACT

This disclosure provides a method of absorbing or discharging water of an ophthalmic medical device capable of absorbing and discharging water, and an ophthalmic medical device. The method of absorbing or discharging water of an ophthalmic medical device of the present disclosure includes using an ophthalmic medical device including a plurality of electrodes, and generating an electroosmotic flow inside and/or outside the medical device.

26 Claims, 10 Drawing Sheets

(51) Int. Cl.
    *A61F 9/007*     (2006.01)
    *A61N 1/32*      (2006.01)
    *G02C 7/04*      (2006.01)

(56) References Cited

FOREIGN PATENT DOCUMENTS

| | | | |
|---|---|---|---|
| JP | 2017198984 | A | 11/2017 |
| JP | 2018502639 | A | 2/2018 |
| JP | 2018530003 | A | 10/2018 |
| WO | 2018194079 | A1 | 10/2018 |

OTHER PUBLICATIONS

Apr. 2, 2019, International Search Report issued in the International Patent Application No. PCT/JP2019/008475.

Joohee Kim et al., Wearable smart sensor systems integrated on soft contact lenses for wireless ocular diagnostics, Nature Communications, 2017, pp. 1-8, vol. 8.

Magnus Falk et al., Miniature Biofuel Cell as a Potential Power Source for Glucose-Sensing Contact Lenses, Analytical Chemistry, 2013, pp. 6342-6348, vol. 85, Issue 13.

Sep. 16, 2021, International Preliminary Report on Patentability issued in the International Patent Application No. PCT/JP2019/008475.

Sep. 19, 2022, the Extended European Search Report issued by the European Patent Office in the corresponding European Patent Application No. 19918200.7.

\* cited by examiner

METHOD OF ABSORBING OR DISCHARGING WATER OF OPHTHALMIC MEDICAL DEVICE AND OPHTHALMIC MEDICAL DEVICE

TECHNICAL FIELD

The present disclosure relates to a method of absorbing or discharging water of an ophthalmic medical device and to an ophthalmic medical device.

BACKGROUND

Tear is a dilute aqueous solution containing lipids and electrolytes (about 98% is water), which forms a liquid film of about 7 μm on the eyeball by blinking from the tear meniscus on the back of the lower eyelid to protect the surface of the eyeball from foreign substances, infections and the like, and also supplies oxygen and nutrients to the cornea. In addition, tear needs to be sufficiently supplied to the surface of the corneal conjunctiva to obtain a clear vision.

Dry eye due to lack of tears causes a decrease in quality of life because of discomfort, and causes inflammation and damage to the surface of the eyeball and visual impairment. However, dry eye has been increasing in recent years due to the popularization of contact lenses. Further, contact lenses were previously contraindicated for dry eye patients, but recently there is a tendency to prescribe contact lenses for patients who have a request even if they have dry eye.

Conventional examples of an attempt to provide a contact lens with a function include an intraocular pressure sensing lens for preventing glaucoma (NPT 1) and a contact lens equipped with a biological battery that generates power with sugar in tears (NPT 2).

CITATION LIST

Non-Patent Literature

NPL 1: Kim, J. et al., Wearable smart sensor systems integrated on soft contact lenses for wireless ocular diagnostics, Nature Communications, 2017, 8, 1-8

NPL 2: Miniature biofuel cell as a potential power source for glucose-sensing contact lenses, M. Falk, V. Andoralov, M. Silow, M. D. Toscano, and S. Shleev, Anal. Chem., 2013, 85, 6342-8

SUMMARY

Technical Problem

However, conventional contact lenses cannot sufficiently absorb water such as tears themselves, and there is a strong demand for the development and improvement of the water absorption technology for contact lenses. Further, there has been a demand for a method of containing a drug or the like in a contact lens and discharging an aqueous solution containing the drug for the purpose of, for example, further suppressing dry eye and treating eye diseases such as a drop in intraocular pressure. In addition to contact lenses, other medical devices, intraocular lenses and the like used for treating eye diseases such as a drop in intraocular pressure are also required to have a function of adjusting water content.

It could thus be helpful to provide a method of absorbing or discharging water of an ophthalmic medical device capable of absorbing and discharging water, and an ophthalmic medical device.

Solution to Problem

We thus provide the following.

[1]
A method of absorbing or discharging water of an ophthalmic medical device, which comprises using an ophthalmic medical device including a plurality of electrodes, and generating an electroosmotic flow either or both inside and outside the ophthalmic medical device.

[2]
The method of absorbing or discharging water of an ophthalmic medical device according to [1], wherein the ophthalmic medical device is an ophthalmic lens.

[3]
The method of absorbing or discharging water of an ophthalmic medical device according to [1] or [2], wherein the ophthalmic medical device is a contact lens.

[4]
The method of absorbing or discharging water of an ophthalmic medical device according to any one of [1] to [3], which comprises using an ophthalmic medical device including a platform and a plurality of electrodes provided in contact with the platform, and generating an electroosmotic flow inside the platform.

[5]
The method of absorbing or discharging water of an ophthalmic medical device according to any one of [1] to [4], wherein the ophthalmic medical device has a fixed charge.

[6]
The method of absorbing or discharging water of an ophthalmic medical device according to [5], wherein an amount of the fixed charge per unit mass of the ophthalmic medical device is 1 C/g to 200 C/g.

[7]
The method of absorbing or discharging water of an ophthalmic medical device according to any one of [1] to [6], wherein the ophthalmic medical device comprises a hydrogel material.

[8]
The method of absorbing or discharging water of an ophthalmic medical device according to [7], wherein
the hydrogel material is a polymer material comprising a unit of monomer having the fixed charge, and
a content of the unit of monomer having the fixed charge in the hydrogel material is 0.1 mass % to 20.0 mass %.

[9]
The method of absorbing or discharging water of an ophthalmic medical device according to [8], wherein the unit of monomer having the fixed charge comprises at least one selected from the group consisting of a sulfonic group, a carboxyl group, a phosphate group, and an amino group.

[10]
The method of absorbing or discharging water of an ophthalmic medical device according to [8] or [9], wherein the unit of monomer having the fixed charge is a unit of methacrylic acid.

[11]
The method of absorbing or discharging water of an ophthalmic medical device according to any one of [1] to [10], wherein the plurality of electrodes is provided at ends of the ophthalmic medical device.

[12]

The method of absorbing or discharging water of an ophthalmic medical device according to any one of [1] to [11], wherein the plurality of electrodes forms a metal/$O_2$ battery.

[13]

The method of absorbing or discharging water of an ophthalmic medical device according to any one of [1] to [12], wherein at least one of the plurality of electrodes is an electrode carrying an enzyme that catalyzes an oxidation-reduction reaction.

[14]

The method of absorbing or discharging water of an ophthalmic medical device according to [13], wherein the enzyme comprises at least one selected from the group consisting of bilirubin oxidase and fructose dehydrogenase.

[15]

An ophthalmic medical device, which comprises a plurality of electrodes and can generate an electroosmotic flow.

[16]

The ophthalmic medical device according to [15], which is an ophthalmic lens.

[17]

The ophthalmic medical device according to [15] or [16], which is a contact lens.

[18]

The ophthalmic medical device according to any one of [15] to [17], which comprises a platform and a plurality of electrodes provided in contact with the platform, and generates an electroosmotic flow between the plurality of electrodes.

[19]

The ophthalmic medical device according to any one of [15] to [18], wherein the ophthalmic medical device has a fixed charge.

[20]

The ophthalmic medical device according to [19], wherein an amount of the fixed charge per unit mass of the ophthalmic medical device is 1 C/g to 200 C/g.

[21]

The ophthalmic medical device according to any one of [15] to [20], wherein the ophthalmic medical device comprises a hydrogel material.

[22]

The ophthalmic medical device according to [21], wherein the hydrogel material is a polymer material containing a unit of monomer having the fixed charge, and a content of the unit of monomer having the fixed charge in the hydrogel material is 0.1 mass % to 20.0 mass %.

[23]

The ophthalmic medical device according to [22], wherein the unit of monomer having the fixed charge comprises at least one selected from the group consisting of a sulfonic group, a carboxyl group, a phosphate group and an amino group.

[24]

The ophthalmic medical device according to [22] or [23], wherein the unit of monomer having the fixed charge is a unit of methacrylic acid.

[25]

The ophthalmic medical device according to any one of [15] to [24], wherein the plurality of electrodes is provided at ends of the ophthalmic medical device.

[26]

The ophthalmic medical device according to any one of [15] to [25], wherein the plurality of electrodes forms a metal/$O_2$ battery.

[27]

The ophthalmic medical device according to any one of [15] to [26], wherein at least one of the plurality of electrodes is an electrode carrying an enzyme that catalyzes an oxidation-reduction reaction.

[28]

The ophthalmic medical device according to [27], wherein the enzyme comprises at least one selected from the group consisting of bilirubin oxidase and fructose dehydrogenase.

Advantageous Effect

The method of absorbing water of an ophthalmic medical device, and the ophthalmic medical device of the present disclosure have the above configurations, and therefore they can absorb and discharge water.

DETAILED DESCRIPTION

Figure 1:
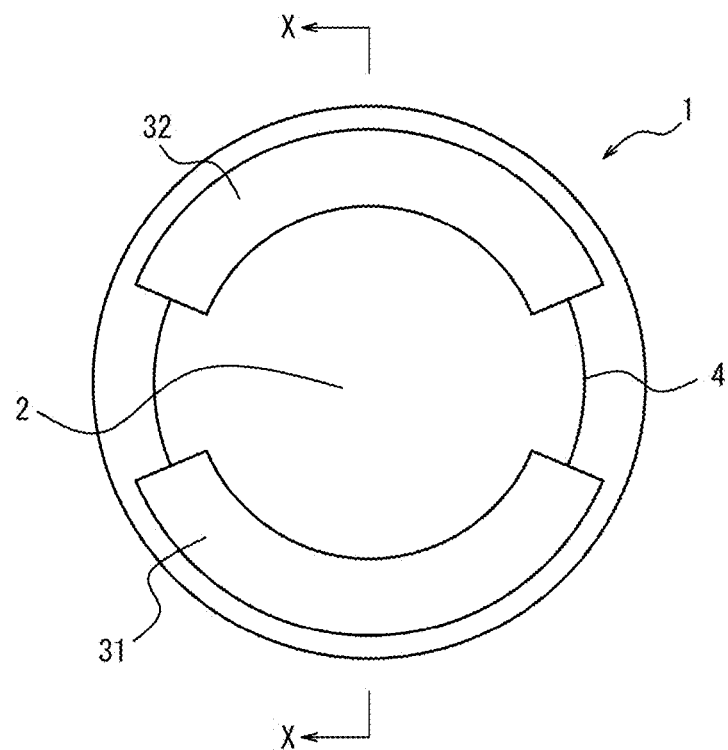
FIG. 1 is a plan view schematically illustrating an example of a contact lens of the present embodiment, where an outer cover 5 covering a lens portion 2 and electrodes 31 and 32 is omitted.

The following describes a method of absorbing or discharging water of a contact lens and a contact lens according to an embodiment of the present disclosure (hereinafter, simply referred to as "the present embodiment") in detail. The present disclosure is not limited to the following description and can be variously modified and implemented within the scope thereof.

The method of absorbing or discharging water of an ophthalmic medical device of the present embodiment includes using an ophthalmic medical device including a plurality of electrodes to generate an electroosmotic flow inside and/or outside the ophthalmic medical device.

[Ophthalmic Medical Device]

The ophthalmic medical device of the present embodiment includes a plurality of electrodes and can generate an electroosmotic flow. The ophthalmic medical device is preferably, for example, a medical device including a platform and a plurality of electrodes provided in contact with the platform to generate an electroosmotic flow between the plurality of electrodes. For example, it is possible to provide a plurality of electrodes (for example, one electrode and the other electrode) in the ophthalmic medical device to generate an electroosmotic flow from one electrode to the other electrode inside and/or outside the medical device.

For example, when the outer surface of the ophthalmic medical device has a positive charge, negatively charged ions in an aqueous solution around the ophthalmic medical device are drawn to the positive electrode, and an electroosmotic flow is generated in which the entire aqueous solution near the outer surface of the ophthalmic medical device flows to the direction of the positive electrode. This makes it possible to retain water on the surface of the ophthalmic medical device and to move the aqueous solution from one electrode toward the other electrode in the ophthalmic medical device.

Further, when the ophthalmic medical device has cavities that serve as flow paths inside a porous body or the like, a positive charge is applied to the surface of the internal flow path to draw negatively charged ions in an aqueous solution inside the ophthalmic medical device to the positive electrode, and an electroosmotic flow is generated in which the entire aqueous solution inside the ophthalmic medical device flows to the direction of the positive electrode. This makes it possible to take in water inside the ophthalmic medical device and discharge the water inside the ophthalmic medical device to the outside.

Examples of the ophthalmic medical device include devices used for prevention and treatment of eye diseases such as ophthalmic lenses like ophthalmic stents, eyeglass, contact lenses, intraocular lenses, and intraocular contact lenses used for micro-invasive glaucoma surgery (MIGS) or the like. It is preferably an ophthalmic lens and more preferably a contact lens.

The ophthalmic medical device has a fixed charge. The amount of the fixed charge per unit mass of the ophthalmic medical device is preferably 1 C/g to 200 C/g from the viewpoint of obtaining an electroosmotic flow having a moderate flow rate for the ophthalmic medical device.

The ophthalmic medical device preferably includes a hydrogel material. From the viewpoint of obtaining an electroosmotic flow having a moderate flow rate as an ophthalmic medical device, the hydrogel material is a polymer material containing a monomer unit having the fixed charge, and the content of the monomer unit having the fixed charge in the hydrogel material is more preferably 0.1 mass % to 20.0 mass %.

From the viewpoint of obtaining an electroosmotic flow having a moderate flow rate as an ophthalmic medical device, the monomer unit having the fixed charge is preferably a monomer unit having at least one group selected from the group consisting of a sulfonic acid group, a carboxyl group, a phosphate group, and an amino group, and is more preferably a methacrylic acid unit.

From the viewpoint of being able to generate an electroosmotic flow throughout the medical device, the plurality of electrodes is preferably provided at the ends of the medical device.

The plurality of electrodes preferably forms a metal/$O_2$ battery. Further, from the viewpoint of excellent biocompatibility, it is preferable that at least one of the plurality of electrodes be an electrode carrying an enzyme that catalyzes an oxidation-reduction reaction. From the viewpoint of being suitable for use as an ophthalmic medical device, it is more preferable that the enzyme contain at least one selected from the group consisting of bilirubin oxidase and fructose dehydrogenase.

(Contact Lens)

As an example of the ophthalmic medical device of the present embodiment, a contact lens will be described below.

Examples of the contact lens include a soft contact lens, a hard contact lens, and a soft/hard hybrid contact lens, among which a soft contact lens is preferred.

FIG. 1 illustrates an example of the contact lens of the present embodiment.

The contact lens 1 includes a plurality of electrodes (one electrode 31 and the other electrode 32), and the electrodes (31, 32) are in contact with the contact lens 1. By applying a voltage to the electrodes (31, 32), an electroosmotic flow is generated in the contact lens 1. It is preferable that one electrode 31 and the other electrode 32 be electrically connected, and for example, they may be electrically connected via a conductive member 4. Note that in the contact lens, the platform is preferably a lens portion 2.

For example, when an electroosmotic flow is generated, water contained in the contact lens flows from one electrode 31 toward the other electrode 32. At that time, water around the contact lens 1 is absorbed from the vicinity of one electrode 31, and water inside the contact lens is discharged from the vicinity of the other electrode 32.

Because the contact lens of the present embodiment energizes the contact lens itself to generate an electroosmotic flow, tears and the like can be taken into the contact lens, and the contact lens can be worn for a long period of time, which provides excellent feeling after use of the contact lens. In addition, it can prevent and suppress dry eye.

The contact lens preferably includes a hydrogel material. The hydrogel material refers to a material that forms a hydrogel by being dispersed in water (dispersion medium). The contact lens may consist only of electrodes and a hydrogel material.

The contact lens preferably has a fixed charge, and the hydrogel material included in the contact lens more preferably has a fixed charge.

Note that the "fixed charge" refers to a charge that is fixed and exists in a region of the ophthalmic medical device (for example, a porous material of the contact lens), and it does not include the charge contained in a substance that flows in and out of the contact lens.

Further, "having a fixed charge" means that the amount per unit mass of the ophthalmic medical device such as a contact lens is 1 C/g or more on average for the entire lens.

The contact lens preferably includes electrodes and a lens portion 2 having a function as a lens. The lens portion is preferably made of a hydrogel material.

Examples of the hydrogel material include natural polymers such as agar, gelatin, agarose, xanthan gum, gellan gum, sclerotiu gum, arabic gum, gum tragacanth, karaya gum, cellulose gum, tamarind gum, guar gum, locust bean gum, glucomannan, chitosan, carrageenan, quince seed, galactan, mannan, starch, dextrin, curdlan, casein, pectin, collagen, fibrin, peptide, chondroitin sulfates such as sodium chondroitin sulfate, hyaluronic acid (mucopolysaccharide) and hyaluronic acid salts such as sodium hyaluronate, alginic acid, alginates such as sodium alginate and calcium alginate, and derivatives thereof; cellulose derivatives such as methyl cellulose, hydroxymethyl cellulose, hydroxyethyl cellulose, hydroxypropyl cellulose, hydroxypropyl methyl cellulose, and carboxymethyl cellulose, and salts thereof; poly (meth) acrylic acids such as polyacrylic acid, polymethacrylic acid, and alkyl acrylate/alkyl methacrylate copolymer, and salts thereof; synthetic polymers such as polyvinyl alcohol, a polymer of polyethylene glycol di (meth) acrylate (PPEGDA, PPEGDM), a homopolymer or copolymer containing a constituent unit derived from hydroxyethyl methacrylate such as polyhydroxyethyl methacrylate, polyacrylamide, poly (N-isopropylacrylamide), poly 2-acrylamide-2-methylpropanesulfonate, poly (N-isopropylacrylamide), a homopolymer or copolymer containing a constituent unit derived from dimethylacrylamide, a homopolymer or copolymer containing a constituent unit derived from vinylpyrrolidone, a copolymer containing a constituent unit derived from dimethylacrylamide, polystyrene sulfonate, polyethylene glycol, carboxyvinyl polymer, alkyl-modified carboxyvinyl polymer, maleic anhydride copolymer, polyalkylene oxide resin, cross-linked product of poly (methyl vinyl ether-alt-maleic anhydride) and polyethylene glycol, polyethylene glycol cross-linked product, N-vinylacetamide cross-linked product, acrylamide cross-linked product, and starch-acrylate graft copolymer cross-linked product; silicone; hydrogel with a interpenetrating network structure and hydrogel with a semi-interpenetrating network structure (DN hydrogel); and a mixture of two or more of these.

Further, the hydrogel material preferably contains a monomer unit having a silicone chain from the viewpoint of improving oxygen permeability. Examples of the monomer having a silicone chain include silicone-containing alkyl (meth) acrylates such as trimethylsiloxydimethylsilylmethyl (meth) acrylate, trimethylsiloxydimethylsilylpropyl (meth) acrylate, methylbis (trimethylsiloxy) silylpropyl (meth) acrylate, tris (trimethylsiloxy) silylpropyl (meth) acrylate, mono [methylbis (trimethylsiloxy) siloxy] bis (trimethylsiloxy) silylpropyl (meth) acrylate, tris [methylbis (trimethylsiloxy) siloxy] silylpropyl (meth) acrylate, methylbis (trimethylsiloxy) silylpropylglyceryl (meth) acrylate, tris (trimethylsiloxy) silylpropylglyceryl (meth) acrylate, mono [methylbis (trimethylsiloxy) siloxy] bis (trimethylsiloxy) silylpropylglyceryl (meth) acrylate, trimethylsilylethyltetramethyldi siloxypropylglyceryl (meth) acrylate, trimethylsilylmethyl (meth) acrylate, trimethylsilylpropyl (meth) acrylate, trimethylsilylpropylglyceryl (meth) acrylate, trimethylsiloxydimethylsilylpropylglyceryl (meth) acrylate, methylbis (trimethylsiloxy) silylethyltetramethyldisiloxymethyl (meth) acrylate, tetramethyltriisopropylcyclotetrasiloxanylpropyl (meth) acrylate, and tetramethyltriisopropylcyclotetrasiloxybis (trimethylsiloxy) silylpropyl (meth) acrylate; silicone-containing styrene derivatives such as tris (trimethylsiloxy) silylstyrene, bis (trimethylsiloxy) methylsilylstyrene, (trimethylsiloxy) dimethylsilylstyrene, tris (trimethylsiloxy) siloxydimethylsilylstyrene, [bis (trimethylsiloxy) methylsiloxy] dimethylsilylstyrene, (trimethylsiloxy) dimethylsilylstyrene, heptamethyltrisiloxanylstyrene, nonamethyltetrasiloxanylstyrene, pentadecamethylheptasiloxanylstyrene, heneikosamethyldecasiloxanylstyrene, heptacosamethyltridecasiloxanylstyrene, hentriacontamethylpentadecasiloxanylstyrene, trimethylsiloxypentamethyldisiloxymethylsilylstyrene, tris (pentamethyldisiloxy) silylstyrene, tris (trimethylsiloxy) siloxybis (trimethylsiloxy) silylstyrene, bis (heptamethyltrisiloxy) methylsilylstyrene, tris [methylbis (trimethylsiloxy) siloxy] silylstyrene, trimethylsiloxybis [tris (trimethylsiloxy) siloxy] silylstyrene, heptakis (trimethylsiloxy) trisilylstyrene, nonamethyltetrasiloxyundecylmethylpentasiloxymethylsilylstyrene, tris [tris (trimethylsiloxy) siloxy] silylstyrene, (tristrimethylsiloxyhexamethyl) tetrasiloxy [tris (trimethylsiloxy) siloxy] trimethylsiloxysilylstyrene, nonakis (trimethylsiloxy) tetrasilylstyrene, bis (tridecamethylhexasiloxy) methylsilylstyrene, heptamethylcyclotetrasiloxanylstyrene, heptamethylcyclotetrasiloxybis (trimethylsiloxy) silylstyrene, tripropyltetramethylcyclotetrasiloxanylstyrene, and trimethylsilylstyrene; silicone-containing diester fumarates such as bis (3-(trimethylsilyl) propylfumarate, bis (3-(pentamethyldisiloxanyl) propyl) fumarate, bis (3-(1,3,3,3-tetramethyl-1-(trimethylsilyl) oxy) disiloxanyl) propyl) fumarate, and bis (tris (trimethylsiloxy) silylpropyl) fumarate.

Furthermore, the hydrogel material may contain a unit of monomer having an ethylenically unsaturated group which is a polymerizable group at both ends from the viewpoint of providing the obtained polymer with a polymer cross-linked structure and excellent physical strength. The monomer having an ethylenically unsaturated group which is a polymerizable group at both ends may be a monomer with an added structure derived from a hydrophilic polymer. Examples of the structure derived from a hydrophilic polymer include polyethylene glycol, polypropylene glycol, polyvinyl alcohol, polyvinylpyrrolidone, poly (meth) acrylic acid, poly (meth) acrylate, poly (2-hydroxyethyl (meth) acrylate), polytetrahydrofuran, polyoxetane, polyoxazoline, polydimethylacrylamide, polydiethylacrylamide, and poly (2-methacryloyloxyethyl phosphorylcholine).

Moreover, the hydrogel material may contain a unit of hydrophilic monomer. Examples of the hydrophilic monomer include (meta) acrylamide; hydroxyalkyl (meth) acrylates such as 2-hydroxyethyl (meth) acrylate, hydroxypropyl (meth) acrylate, and hydroxybutyl (meth) acrylate; (alkyl) aminoalkyl (meth) acrylates such as 2-dimethylaminoethyl (meth) acrylate and 2-butylaminoethyl (meth) acrylate; alkylene glycol mono (meth) acrylates such as ethylene glycol mono (meth) acrylate and propylene glycol mono (meth) acrylate; polyalkylene glycol mono (meth) acrylates such as polyethylene glycol mono (meth) acrylate and polypropylene glycol mono (meth) acrylate; ethylene glycol allyl ether; ethylene glycol vinyl ether; (meth) acrylic acid; aminostyrene; hydroxystyrene; vinyl acetate; glycidyl (meth) acrylate; allyl glycidyl ether; vinyl propionate; N, N-dimethylmethacrylamide, N, N-diethylmethacrylamide, N-(2-hydroxyethyl) methacrylamide, N-isopropylmethacrylamide, methacryloylmorpholine; N-vinyl lactam such as N-vinyl-2-pyrrolidone, N-vinyl-3-methyl-2-pyrrolidone, N-vinyl-4-methyl-2-pyrrolidone, N-vinyl-5-methyl-2-pyrrolidone, N-vinyl-6-methyl-2-pyrrolidone, N-vinyl-3-ethyl- 2-pyrrolidone, N-vinyl-4,5-dimethyl-2-pyrrolidone, N-vinyl-5,5-dimethyl-2-pyrrolidone, N-vinyl-3,3,5-trimethyl-2-pyrrolidone, N-vinyl-2-piperidone, N-vinyl-3-methyl-2-piperidinone, N-vinyl-4-methyl-2-piperidinone, N-vinyl-5-methyl-2-piperidinone, N-vinyl-6-methyl-2-piperidinone, N-vinyl-6-ethyl-2-piperidinone, N-vinyl-3,5-dimethyl-2-piperidinone, N-vinyl-4,4-dimethyl-2-piperidinone, N-vinyl-2-caprolactam, N-vinyl-3-methyl-2-caprolactam, N-vinyl-4-methyl-2-caprolactam, N-vinyl-7-methyl-2-caprolactam, N-vinyl-7-ethyl-2-caprolactam, N-vinyl-3,5-dimethyl-2-caprolactam, N-vinyl-4,6-dimethyl-2-caprolactam, and N-vinyl-3,5,7-trimethyl-2-caprolactam; and N-vinylamide such as N-vinylformamide, N-vinyl-N-methylformamide, N-vinyl-N-ethylformamide, N-vinylacetamide, N-vinyl-N-methylacetamide, N-vinyl-N-ethylacetamide, and N-vinylphthalimide.

Also, from the viewpoint of adjusting the hardness of the contact lens to make it hard or soft, the hydrogel material may contain a unit derived from a hardness adjusting monomer such as linear, branched or cyclic alkyl (meth) acrylates such as methyl (meth) acrylate, ethyl (meth) acrylate, isopropyl (meth) acrylate, n-propyl (meth) acrylate, isobutyl (meth) acrylate, n-butyl (meth) acrylate, 2-ethylhexyl (meth) acrylate, n-octyl (meth) acrylate, n-decyl (meth) acrylate, n-dodecyl (meth) acrylate, t-butyl (meth) acrylate, pentyl (meth) acrylate, t-pentyl (meth) acrylate, hexyl (meth) acrylate, heptyl (meth) acrylate, nonyl (meth) acrylate, stearyl (meth) acrylate, cyclopentyl (meth) acrylate, and cyclohexyl (meth) acrylate; alkoxyalkyl (meth) acrylates such as 2-ethoxyethyl (meth) acrylate, 3-ethoxypropyl (meth) acrylate, 2-methoxyethyl (meth) acrylate, and 3-methoxypropyl (meth) acrylate; alkylthioalkyl (meth) acrylate such as ethylthioethyl (meth) acrylate and methylthioethyl (meth) acrylate; styrene; α-methylstyrene; alkylstyrene such as methylstyrene, ethylstyrene, propylstyrene, butylstyrene, t-butylstyrene, isobutylstyrene, and pentylstyrene; and alkyl-α-methylstyrene such as methyl-α-methylstyrene, ethyl-α-methylstyrene, propyl-α-methylstyrene, butyl-α-methylstyrene, t-butyl-α-methylstyrene, isobutyl-α-methylstyrene, and pentyl-α-methylstyrene. The unit of hardness adjusting monomer is preferably 1 mass % to 30 mass % and more preferably 3 mass % to 20 mass % with respect to 100 mass % of the hydrogel material.

Among the above, a copolymer containing a constituent unit derived from hydroxyethyl methacrylate, a copolymer containing a constituent unit derived from vinylpyrrolidone, a copolymer containing a constituent unit derived from dimethylacrylamide, and polyvinyl alcohol are preferred from the viewpoint of being suitable for use as a contact lens, and a copolymer containing hydroxyethyl methacrylate as a constituent unit is more preferred from the viewpoint of obtaining a hydrogel material having pores particularly suitable for water absorption and discharge of contact lenses.

These may be used alone or in combination of two or more.

Examples of the hydrogel material having a fixed charge include a gel material in which a functional group having a fixed charge has been introduced into a hydrogel material having no fixed charge, and a gel material that is a polymer containing a unit of monomer having a fixed charge, among which a gel material that is a polymer containing a unit of monomer having a fixed charge is preferred, and a copolymer of a non-chargeable monomer and a monomer having a fixed charge is more preferred. The fixed charge may be a positive charge and/or a negative charge as long as the amount of either the positive charge or the negative charge is large, but it is preferably either a positive charge or a negative charge.

The unit of monomer having a fixed charge is preferably a unit of monomer having a negative charge. It is more preferably a unit derived from a monomer containing at least one selected from the group consisting of a sulfonic group, a carboxyl group, a phosphate group and an amino group, or a unit derived from a salt thereof. From the viewpoint of obtaining an electroosmotic flow suitable for use as a contact lens, it is more preferably a unit derived from a monomer containing a sulfonic group or a carboxyl group or a unit derived from a salt thereof, and particularly preferably a unit derived from a monomer containing a carboxyl group or a unit derived from a salt thereof.

The unit of monomer having a fixed charge is preferably a unit of monomer having at least one selected from the group consisting of a sulfonic group, a carboxyl group, a phosphate group, and an amino group, more preferably a unit of monomer having a sulfonic group or a carboxyl group, and further preferably a unit of monomer having a carboxyl group.

Examples of the non-chargeable monomer include hydroxyethyl methacrylate, ethylene glycol diacrylate, methyl methacrylate, N-vinylpyrrolidone, dimethylacrylamide, glycerol methacrylate, and vinyl alcohol.

The non-chargeable monomer may be used alone or in combination of two or more.

From the viewpoint of providing the contact lens with even better strength and flexibility, it is preferable that the non-chargeable monomer of the hydrogel material be hydroxyethyl methacrylate, and the content of the unit of hydroxyethyl methacrylate be 78 mass % to 93 mass % with respect to 100 mass % of the hydrogel material.

Examples of the monomer having a fixed charge include carboxyl group-containing monomers such as acrylic acid, methacrylic acid, itaconic acid, succinic acid 1-(2-methacryloyloxyethyl), βcarboxyethyl acrylate, itaconic acid, maleic acid, fumaric acid, crotonic acid, and isocrotonic acid; sulfonic group-containing monomers such as 2-acrylamide-2-methyl-propanesulfonic acid, styrene sulfonic acid, vinyl sulfonic acid, (meth) acrylic sulfonic acid, (meth) acrylamide propane sulfonic acid, sulfopropyl (meth) acrylate, and (meth) acryloyloxynaphthalene sulfonic acid; phosphate group-containing monomers such as 2-hydroxyethyl acryloyl phosphate; amino group-containing monomers such as (alkyl) aminoalkyl (meth) acrylates such as 2-dimethylaminoethyl (meth) acrylate, 2-butylaminoethyl (meth) acrylate and aminoethyl (meth) acrylate, and aminostyrene; and salts thereof. Among these, methacrylic acid and styrene sulfonic acid are preferred from the viewpoint of being able to generate an electroosmotic flow having a flow rate suitable for use as a contact lens.

The monomer having a fixed charge can be used alone or in combination of two or more.

From the viewpoints of being able to apply a fixed charge that can generate an electroosmotic flow with a moderate flow rate inside the contact lens and providing the contact lens with moderate strength and flexibility, the content of the unit of monomer having a fixed charge in the hydrogel material is preferably 0.1 mass % to 20 mass %, more preferably 2 mass % to 15 mass %, and still more preferably 3 mass % to 10 mass % with respect to 100 mass % of the hydrogel material.

The polymer in the hydrogel material can be obtained by, for example, adding a polymerization initiator, a crosslinking agent, a polymerization accelerator and the like to a mixed solution of monomers containing the monomers constituting the hydrogel material, the monomer having a fixed charge and the like, and polymerizing the mixture.

Examples of the polymerization initiator include peroxides such as lauroyl peroxide, cumene hydroperoxide and benzoyl peroxide, which are common radical polymerization initiators, azobisvaleronitrile such as 2,2'-azobis (2,4 dimethylvaleronitrile) (V-65), and azobisisobutyronitrile (AIBN).

Examples of the cross-linking agent include allyl methacrylate, vinyl methacrylate, 4-vinylbenzyl methacrylate, 3-vinylbenzyl methacrylate, methacryloyloxyethyl acrylate, ethylene glycol dimethacrylate, diethylene glycol dimethacrylate, diethylene glycol diallyl ether, triethylene glycol dimethacrylate, tetraethylene glycol dimethacrylate, propylene glycol dimethacrylate, dipropylene glycol dimethacrylate, butanediol dimethacrylate, trimethylolpropane trimethacrylate, 2,2-bis (p-methacryloyloxyphenyl) hexafluoropropane, 2,2-bis (m-methacryloyloxyphenyl) hexafluoropropane, 2,2-bis (o-methacryloyloxyphenyl) hexafluoropropane, 2,2-bis (p-methacryloyloxyphenyl) propane, 2,2-bis (m-methacryloyloxyphenyl) propane, 2,2-bis (o-methacryloyloxyphenyl) propane, 1,4-bis (2-methacryloyloxyhexafluoroisopropyl) benzene, 1,3-bis (2-methacryloyloxyhexafluoroisopropyl) benzene, 1,2-bis (2-methacryloyloxyhexafluoroisopropyl) benzene, 1,4-bis (2-methacryloyloxyisopropyl) benzene, 1,3-bis (2-methacryloyloxyisopropyl) benzene, and 1,2-bis (2-methacryloyloxyisopropyl) benzene. The cross-linking agent is preferably 1 part by mass or less and more preferably 0.8 parts by mass or less, and preferably 0.05 parts by mass or more and more preferably 0.1 parts by mass or more with respect to 100 parts by mass of the total amount of the monomers used for the polymerization.

The hydrogel material can be obtained with, for example, a method of solidifying a gel solution, and a method of placing the mixed solution of monomers described above in a mold for contact lens of metal, glass, plastic or the like, sealing the mold, and raising the temperature gradually or continuously in a range of 25° C. to 120° C. in a constant temperature bath or the like, and performing polymerization for 5 hours to 120 hours.

During the polymerization, ultraviolet rays, electron beams, gamma rays and the like may be used. Further, solution polymerization may be applied by adding water or an organic solvent to the mixed solution of monomers.

After the polymerization, the mixture is cooled to room temperature, and the obtained molded piece is taken out from the mold and, if necessary, cut and polished. The obtained contact lens may be hydrated and swollen to form a hydrogel. Examples of the liquid used for hydration and swelling (swelling liquid) include water contained in the contact lens described later. It is possible to heat the swelling liquid to 60° C. to 100° C. and immerse the contact lens in the swelling liquid for a certain period to quickly bring it into a hydrated and swollen state. In addition, unreacted monomers contained in the polymer can be removed by the swelling treatment.

Examples of the water contained in the contact lens include an aqueous solution containing ions having a charge opposite to the fixed charge, from the viewpoint of generating an electroosmotic flow.

Examples of anion contained in the aqueous solution include amino acid ion (natural amino acid ion and unnatural amino acid ion), chloride ion, citrate ion, lactate ion, succinate ion, phosphate ion, malate ion, pyrrolidone carboxylate ion, sulfocarbolate ion, sulfate ion, nitrate ion, phosphate ion, carbonate ion, and perchlorate ion. Examples of the natural amino acid include glycine, alanine, valine, leucine, isoleucine, phenylalanine, tyrosine, threonine, serine, proline, tryptophan, methionine, cysteine, aspartic acid, glutamic acid, asparagine, glutamine, lysine, arginine, and histidine. Examples of the unnatural amino acid include hydroxyproline, cystine, and thyroxine.

Examples of cation contained in the aqueous solution include $K^+$, $Na^+$, $Ca^{2+}$, and $Mg^{2+}$.

Examples of the aqueous solution include a tear solution, an artificial tear solution, a physiological saline solution, and a Ringer's solution. The aqueous solution may contain a drug.

From the viewpoint of being able to generate an electroosmotic flow with a moderate flow rate inside the contact lens, the amount of fixed charge per unit mass of the contact lens is preferably 1 C/g to 200 C/g, more preferably 20 C/g to 150 C/g, and still more preferably 30 C/g to 100 C/g.

In the present specification, the amount of fixed charge per unit mass can be measured by a zeta potential measuring device or the like.

The thickness of the contact lens is preferably 0.05 mm to 0.20 mm.

—Electrode—

The contact lens 1 has a plurality of electrodes, at least a part of which are in contact with the contact lens. The number of the electrodes may be two or more, but it is preferably two, that is, a positive electrode and a negative electrode.

It is preferable that the plurality of electrodes be electrically connected to each other.

Figure 2:
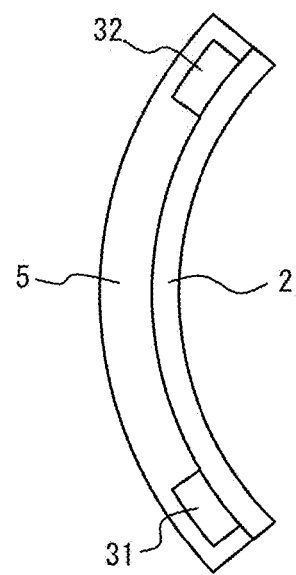
FIG. 2 is a cross-sectional view along the line X-X of FIG. 1, which also illustrates the outer cover 5 omitted in FIG. 1.
Figure 3:
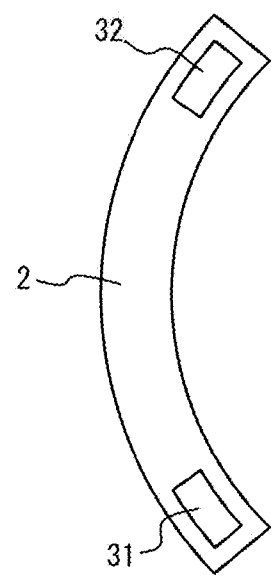
FIG. 3 is a cross-sectional view schematically illustrating another example of a contact lens of the present embodiment.

The electrodes may be provided on the surface of the contact lens (FIG. 2) or may be embedded inside the contact lens (for example, inside the hydrogel material of the lens portion 2) (FIG. 3). When the electrodes are provided on the surface of the contact lens, the electrode surface may be covered with an outer surface cover 5 from the viewpoint of protecting the surface of the eyeball and the back of the eyelid.

The electrodes are preferably provided at the end of the contact lens from the viewpoint of being able to generate an electroosmotic flow throughout the contact lens. For example, in a line segment along the contact lens surface that passes through the center of the contact lens surface and connects one end to the other end, it is possible to provide one electrode 31 at any position 0% to 30% from one end and provide the other electrode 32 at any position 0% to 30% from the other end with respect to 100% the total length of the line segment.

Figure 4:
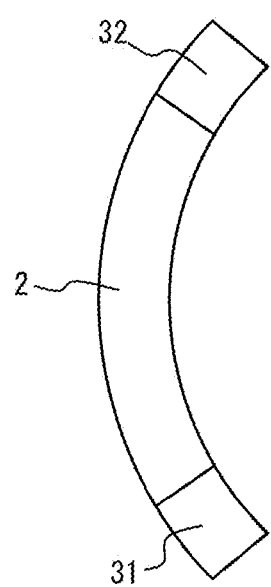
FIG. 4 is a cross-sectional view schematically illustrating another example of a contact lens of the present embodiment.

The electrodes may be provided on the surface of the contact lens (FIG. 2) or may be provided on the side surface of the contact lens from the viewpoint of retaining water throughout the lens and further improving the tear absorption efficiency by arranging the electrodes closer to the tear meniscus and the lacrimal gland (FIG. 4). The words "provided on the side surface of the contact lens" mean that they are provided at a position 0% from one end or the other end described above.

The plurality of electrodes may be provided at positions whose distances from the center of the contact lens are same or positions whose distances from the center of the contact lens are different.

Examples of the electrode include a metal electrode and a bioelectrode. Among these, one electrode is preferably an oxygen electrode, and the cathode is preferably an oxygen electrode.

Examples of the electrode material include carbon materials such as carbon nanotube, Ketjen black, glassy carbon, graphene, fullerene, carbon fiber, carbon fabric, and carbon aerogel; conductive polymers such as polyaniline, polyacetylene, polypyrrole, poly (p-phenylene vinylene), polythiophene, and poly (p-phenylene sulfide); semiconductors such as silicone, germanium, indium tin oxide (ITO), titanium oxide, copper oxide, and silver oxide; and metals such as gold, platinum, titanium, aluminum, tungsten, copper, iron and palladium.

Examples of a combination of a positive electrode (cathode) and a negative electrode (anode) include a combination of a metal electrode and an oxygen electrode (metal/oxygen battery) such as a combination of aluminum and a carbon electrode (CF/CNT, electrode with carbon nanotubes modified on carbon fabric).

The electrode preferably contains at least one electrode carrying an enzyme that catalyzes an oxidation-reduction reaction.

Examples of the enzyme that catalyzes a reduction reaction carried by the positive electrode (cathode) include bilirubin oxidase (BOD), glucose oxidase, glucose dehydrogenase, amino acid oxidase, lactate oxidase, laccase, Cu efflux oxidase (Cueo), and ascorbate oxidase. In particular, bilirubin oxidase (BOD) is preferred from the viewpoint of enabling long-term absorption and discharge of water and generating a moderate electroosmotic flow inside the lens.

Examples of the enzyme that catalyzes an oxidation reaction carried by the negative electrode (anode) include fructose dehydrogenase (D-fructose dehydrogenase, FDH), glucose oxidase, glucose dehydrogenase (GDH), alcohol oxidase, alcohol dehydrogenase, lactate oxidase, and lactate dehydrogenase. Fructose dehydrogenase (FDH) is particularly preferred from the viewpoint of simplifying the enzyme reaction system because no mediator (coenzyme) is required.

The enzyme preferably contains at least one selected from the group consisting of bilirubin oxidase and fructose dehydrogenase, and a combination of an electrode containing BOD and an electrode containing FDH is preferred. A combination of BOD and FDH is particularly preferred because it can exhibit high activity near pH 5.

Note that these enzymes that catalyze a reduction reaction may be used alone or in combination of two or more.

—Conductive Member—

Examples of the material of the conductive member 4 include carbon materials such as carbon nanotube, Ketjen black, glassy carbon, graphene, fullerene, carbon fiber, carbon fabric, and carbon aerogel; conductive polymers such as polyaniline, polyacetylene, polypyrrole, poly (p-phenylene vinylene), polythiophene, and poly (p-phenylene sulfide); semiconductors such as silicone, germanium, indium tin oxide (ITO), titanium oxide, copper oxide, and silver oxide; and metals such as gold, platinum, titanium, aluminum, tungsten, copper, iron, palladium, and stainless steel. In particular, a conductive polymer is preferred from the viewpoint of flexibility, biocompatibility and the like. These may be used alone or in combination of two or more.

The conductive member 4 may be electrically connected between the electrodes through the surface or the inside of the contact lens, or may be connected to a power source outside the contact lens. The external power source may be connected via an inductor or a capacitor.

For example, the conductive member 4 may be a circuit made of a conductive polymer formed on the surface of the lens portion 2 using a printing technique.

—Outer Cover—

The outer surface cover 5 may be provided only on the surface of the electrodes or may be provided throughout the surface of the lens (FIG. 2).

The outer surface cover preferably has flexibility and biocompatibility with the outer surface of a biological tissue 50. Examples of a hydrogel used for the outer surface cover include the same hydrogel materials as those of the contact lens described above. The outer surface cover may have the same composition as the hydrogel material of the contact lens or may have a different composition. The hydrogel of the outer surface cover may be used alone or in combination of two or more.

The electrodes (31, 32) and the conductive member 4 may be provided, for example, by impregnating the electrodes and the conductive member in a gel solution or a monomer solution and then solidifying or polymerizing them, or they may be provided by placing the electrodes and the conductive member on the surface of the contact lens and covering them with an outer cover.

The contact lens of the present embodiment can be used as a contact lens to be worn on the eye of a human or a mammal other than human, for example.

(Ophthalmic Stent)

Other examples of the ophthalmic medical device include an ophthalmic stent.

Examples of the ophthalmic stent include a stent including a platform and a plurality of electrodes provided in contact with the platform to generate an electroosmotic flow between the plurality of electrodes.

The shape of the ophthalmic stent may be, for example, a columnar shape, a conical shape, a polygonal columnar shape, a polygonal pyramid shape, a spherical shape, or a combined shape thereof. The ophthalmic stent may have a bent structure. The cross-sectional shape of the ophthalmic stent may be an ellipse, a circle, a polygon or the like. All the cross-sections may have the same shape or different shapes. The ophthalmic stent may be provided with an external protrusion so that the stent hardly shifts from the insertion position after insertion. The ophthalmic stent is preferably hollow, and the hollow more preferably penetrates from one end to the other end. The ophthalmic stent preferably has a cylindrical portion and may consist of only the cylindrical portion. The ophthalmic stent may have a cylindrical portion with an outer diameter of 50 μm to 500 μm and a length of 0.1 mm to 5 mm.

The ophthalmic stent may have a mesh-like surface with holes on the outer surface or may have no holes on the surface.

The platform of the ophthalmic stent may be made of metal or resin. Examples of the metal include shape memory alloys that obtain shape memory effect and super elasticity through heat treatment such as nickel (Ni)—Ti alloy, copper (Cu)-zinc (Zn)—X (X=aluminum (Al), iron (Fe), etc.) alloy, and Ni—Ti—X (X=Fe, Cu, vanadium (V), cobalt (Co), etc.) alloy; stainless steel, tantalum (Ta), titanium (Ti), platinum (Pt), gold (Au), and tungsten (W). Examples of the resin include polyolefin resin, polyester resin, polyamide resin, polyurethane resin, and silicone resin. For the platform and the electrodes, the metal may be covered with the resin. Further, the platform and the electrodes may be coated with heparin or the like or may be coated with a drug having a fixed charge (for example, a drug having an anticoagulant effect).

The platform of the ophthalmic stent preferably has a fixed charge. From the viewpoint of generating an electroosmotic flow throughout the ophthalmic stent, it is preferable to provide a site having a fixed charge continuously from one end to the other end of the platform. In a case where the platform is cylindrical, it is preferable that the entire inner surface of the cylinder have a fixed charge.

The amount of the fixed charge per unit mass of the stent is preferably 1 C/g to 200 C/g.

The ophthalmic stent preferably includes a hydrogel material and more preferably includes a portion made of a hydrogel material in the platform. Examples of the hydrogel material include the same hydrogel materials as those of the contact lens described above. In a case where the ophthalmic stent is cylindrical, it is preferable that the entire inner surface of the cylinder is made of a hydrogel material.

The ophthalmic stent has a plurality of electrodes, at least a part of which are provided in contact with the platform. The number of electrodes may be two or more, but it is preferably two, that is, a positive electrode and a negative electrode. It is preferable that the plurality of electrodes be electrically connected to each other.

The electrodes may be provided on the surface of the platform or may be embedded inside the platform.

For example, in a case where the ophthalmic stent is cylindrical, the electrodes are preferably provided near the upper surface and near the bottom surface, and the electrodes are more preferably provided on the inner wall surface of the cylinder on the upper surface and the inner wall surface of the cylinder on the bottom surface or on the side surface of the upper surface and the side surface of the bottom surface.

Examples of the electrodes of the ophthalmic stent include the same electrodes as those of the contact lens described above.

In the ophthalmic stent, the plurality of electrodes may be electrically connected via a conductive member. Examples of the conductive member include the same conductive members as those of the contact lens described above.

The ophthalmic stent may be used as a stent to be inserted into the eye of a human or a mammal other than human, and it may be used as a stent to be inserted into Schlemm's canal, for example.

For example, in a case where a negative charge is fixed on the inner surface of the cylinder and a positive electrode is provided at one end and a negative electrode is provided at the other end, the ophthalmic stent can generate an electroosmotic flow in which an aqueous solution around the ophthalmic stent flows toward the negative electrode on the inner surface of the ophthalmic stent. In this way, the aqueous humor or the like accumulated in the eye can be discharged, and an aqueous solution can be injected from outside of the eye to inside of the eye, for example.

[Absorption and/or Discharge of Water of Ophthalmic Medical Device]

The absorption and/or discharge of water of the ophthalmic medical device of the present embodiment is achieved by using the ophthalmic medical device including a plurality of electrodes to generate an electroosmotic flow inside and/or outside the ophthalmic medical device.

A case of a contact lens will be described below as an example.

(Absorption and/or Discharge of Water of Contact Lens)

The direction in which the aqueous solution flows can be adjusted, for example, by the type of the fixed charge, the arrangement of the negative electrode and the positive electrode, and the like. Further, the electroosmotic flow can be adjusted by, for example, the porosity of the hydrogel material, the amount of the fixed charge of the hydrogel material, the charge concentration of the aqueous solution, the voltage applied between the electrodes, the type of electrode, and the like.

Figure 7A:
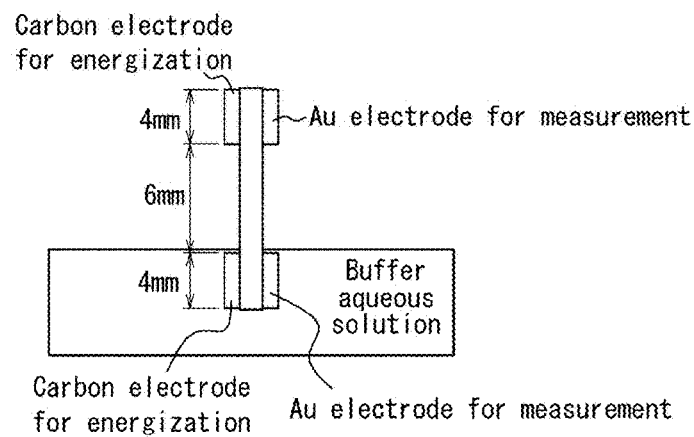
FIG. 7A illustrates an experimental system of the test of Example 3.
Figure 7B:
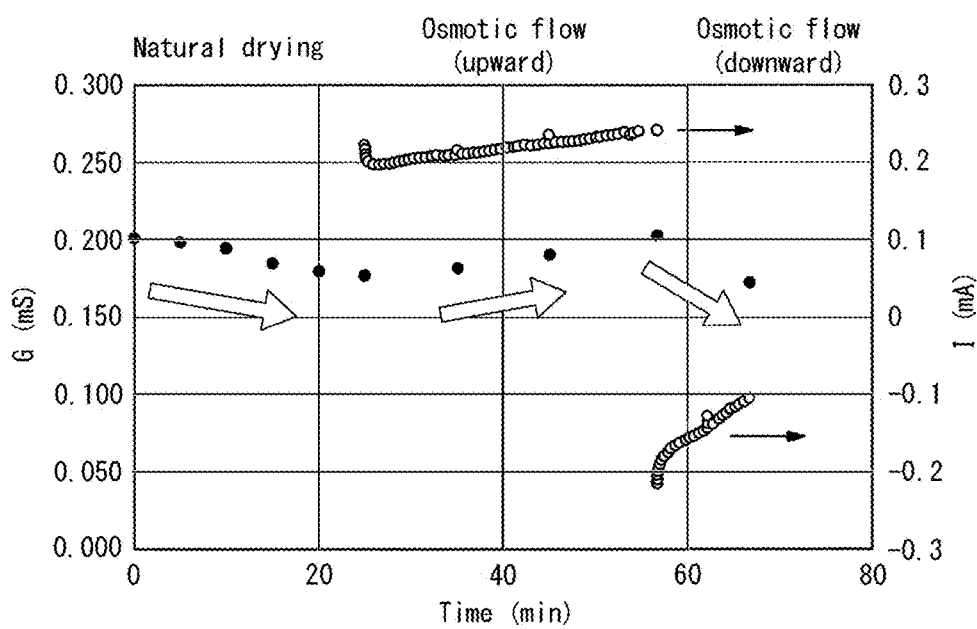
FIG. 7B illustrates the result of Example 3, which is the result of examining the change in conductivity by generating an electroosmotic flow in an order of natural drying, upward electroosmotic flow (0.2 mA), and downward electroosmotic flow (−0.2 mA)

We have found that the electroosmotic flow inside the lens decreases as the lens dries (Example 3, FIG. 7B). For example, the electroosmotic flow can be adjusted by increasing the water content of the lens by, for example, adding an artificial tear solution to the lens.

Figure 5A:
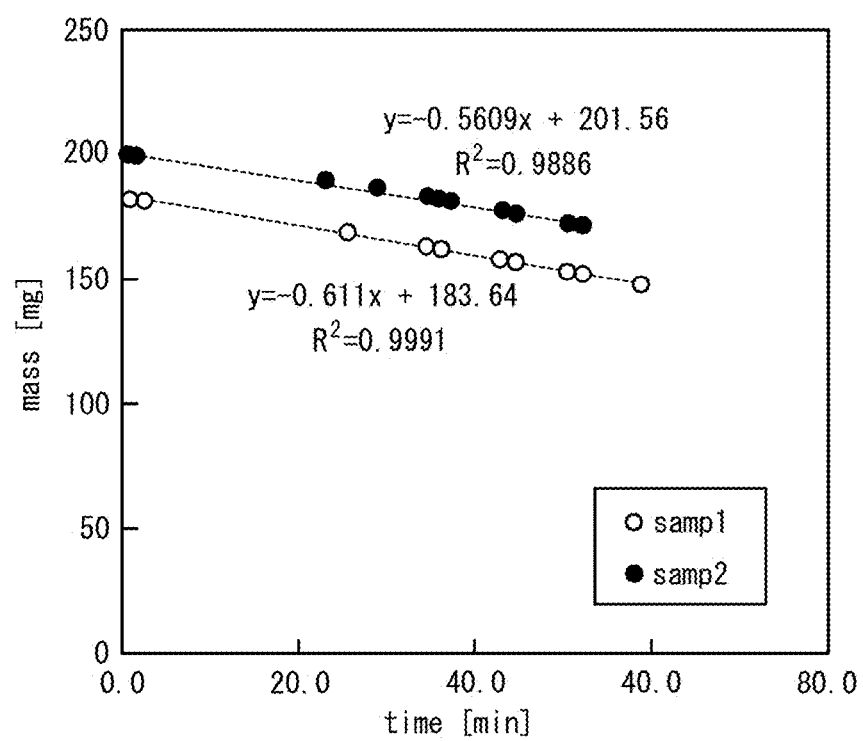
FIG. 5A illustrates the result of Example 1 of weight change during natural drying.
Figure 5B:
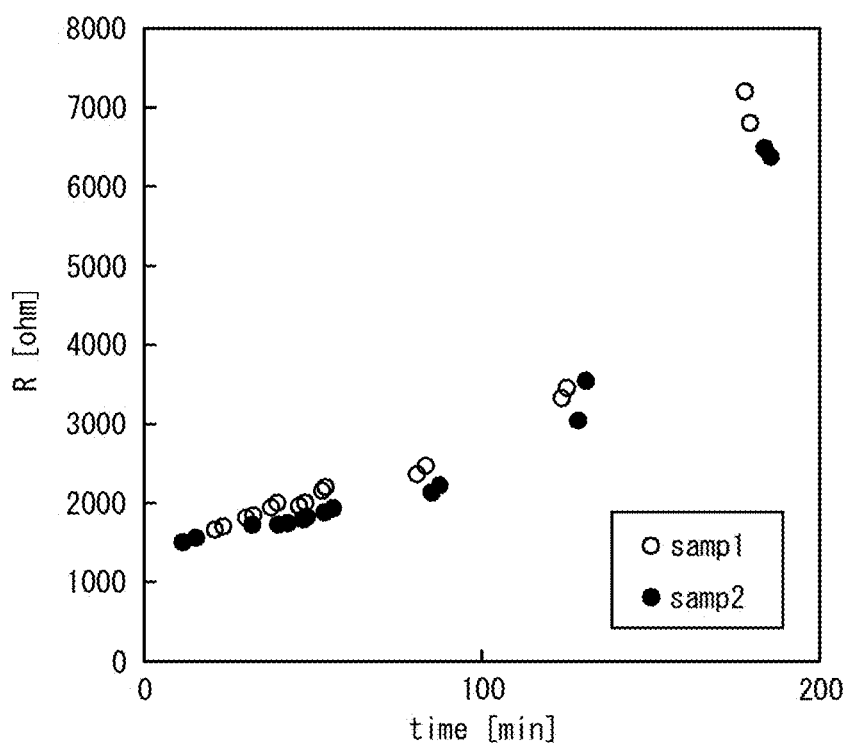
FIG. 5B illustrates the result of Example 1 of resistance change during natural drying.
Figure 5C:
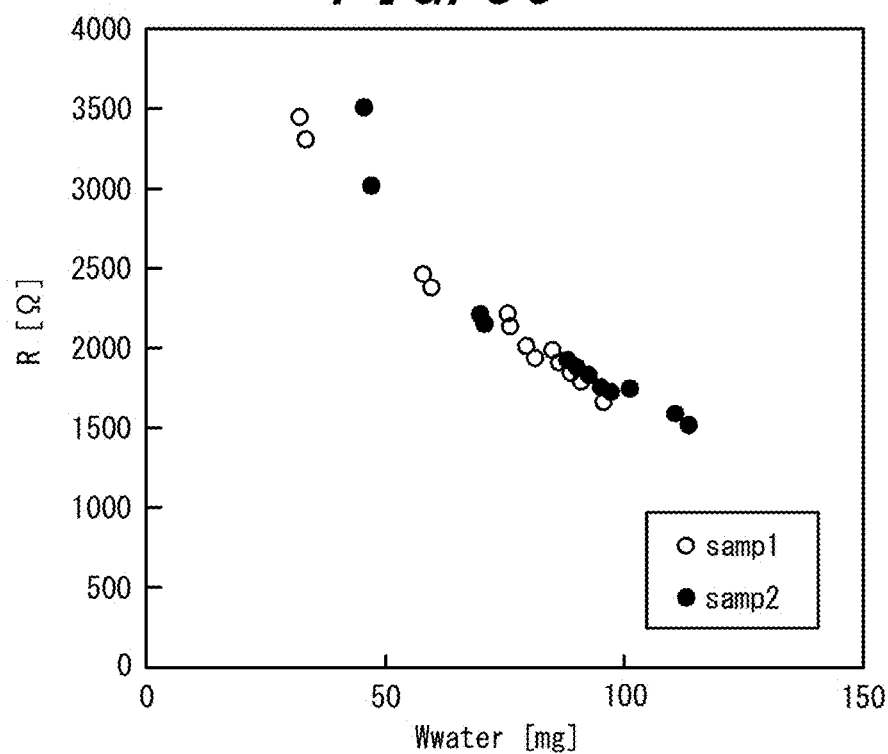
FIG. 5C illustrates the relationship between the water content and the resistance of Example 1.
Figure 5D:
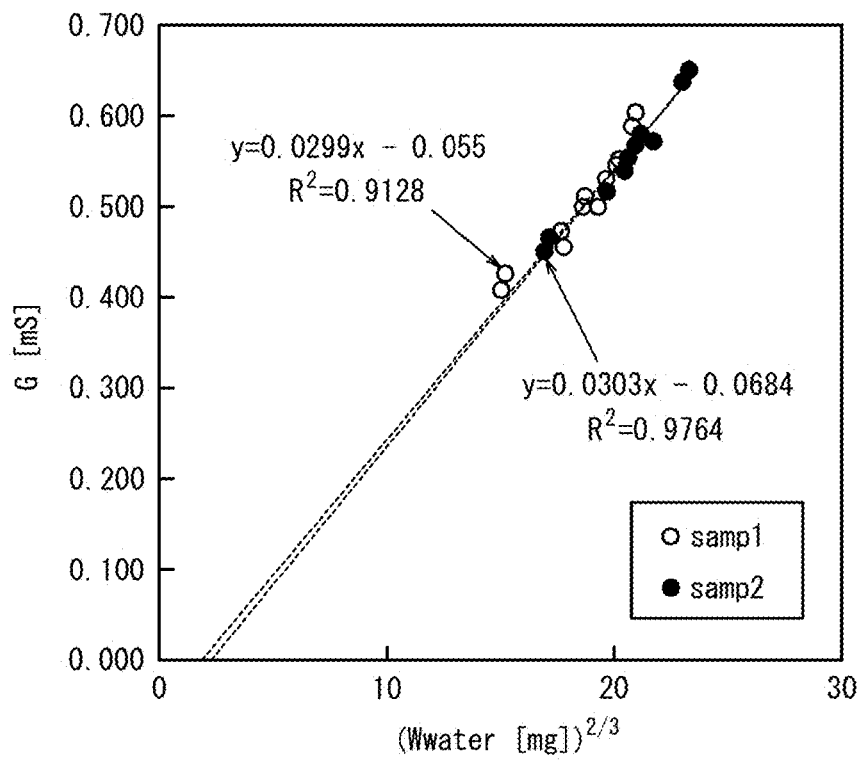
FIG. 5D illustrates the relationship between the water content and the conductivity of Example 1.

We have found that there is a proportional relationship between the water content inside the contact lens and the conductivity (Example 1, FIG. 5D). For example, the electroosmotic flow inside the lens can be understood by measuring the conductivity of the contact lens.

It is preferable to introduce electric current between the plurality of electrodes in the contact lens.

A constant voltage may be applied by direct current between the plurality of electrodes, or a fluctuating voltage may be applied between the plurality of electrodes. Among the above, from the viewpoint of use for a contact lens, the voltage is preferably 1.5 V or less and more preferably 10 mV to 800 mV.

The electroosmotic flow inside the contact lens may be generated continuously or intermittently.

EXAMPLES

The following describes the present disclosure in more detail based on Examples, but the present disclosure is not limited to these Examples.

(Reagent, Material, Etc. Used)

Fructose dehydrogenase (D-fructose dehydorogenase, FDH, from Gluconobactor, EC 1.1.99.11, 20 U mg$^{-1}$, Mw: ca. 140000, Toyobo enzyme)

Bilirubin oxidase (Bilirubin oxidase, product name BO Amano 3, BOD from *Myrothecium* sp. EC 1.3.3.5, 2.39 U/mg, Mw: ca. 68000, Amano)

D-fructose (D(+)-fructose, Mw: 180.16, 127-02765, Wako)

Carbon fabric (Carbon fabric, TCC-3250, provided by Toho Tenax)

Carbon nanotube (Carbon nanotube, C 70 P, provided by Bayer MaterialScience)

Isopropanol ($C_3H_8O$/Isopropyl alcohol, Mw: 60.10, 166-04831, Wako)

Potassium dihydrogenphosphate ($KH_2PO_4$/Potassium dihydrogenphosphate, Mw: 136.09, 169-04245, Wako)

Dipotassium hydrogenphosphate ($K_2HPO_4$/Dipotassium hydrogenphosphate, Mw: 174.2, 164-04315, Wako)

Sodium hydroxide (NaOH/Sodium hydroxide, Mw: 40, 194-09575, Wako)

Citric acid

Disodium hydrogenphosphate

Phosphate buffered saline (0.01 mol/l Phosphate Buffered Saline, 164-18541, Wako)

McIlvaine buffer (McIlvaine buffer, 100 mM: pH 5.0, 150 mM: pH 7.0)

Phosphate buffer solution (Phosphate buffer solution, PBS, 50 mM, pH 7.0)

Low-melting point agarose

Porcine eyeball (provided by Sendai Central Meat Market)

Example 1

—Preparation of Copolymers S1 to S5—

A copolymer S1 is obtained by polymerizing 92 mass % of 2-hydroxyethyl methacrylate (HEMA, non-chargeable monomer), 2 mass % of methacrylic acid (MA), 0.2 mass % of ethylene glycol diacrylate (EDMA), and 3 mass % of methyl methacrylate (MMA) with 0.1 mass % of V-65 as a polymerization initiator, performing elution treatment with water, performing neutralization treatment and then Na chlorination, and then performing sterilization treatment.

Copolymers S2 to S5 can be obtained in the same manner as the copolymer S1 except that the blending amounts of the monomers are as listed in Table 1. The amount of fixed electrolysis per unit mass of the copolymers S1 to S5 is about 20 C g for the copolymer S1, about 50 C/g for the copolymer S2, about 70 C/g for the copolymer S3, about 100 C/g for the copolymer S4, and about 150 C/g for the copolymer S5.

|  |  | Copolymer S1 | Copolymer S2 | Copolymer S3 | Copolymer S4 | Copolymer S5 |
| --- | --- | --- | --- | --- | --- | --- |
| HEMA | mass % | 95 | 92 | 90 | 80 | 70 |
| MA | mass % | 2 | 5 | 7 | 10 | 15 |
| EDMA | mass % | 0.2 | 0.2 | 0.5 | 0.5 | 0.2 |
| MMA | mass % | 3 | 3 | 3 | 10 | 15 |
| V-65 | mass % | 0.1 | 0.1 | 0.1 | 0.1 | 0.1 |

—Water Content and Conductivity—

A rectangular parallelepiped-shaped molded piece having a thickness of 2 mm, a long side of 14 mm and a short side of 7.5 mm was prepared using the copolymer S2 described above. The relationship between the water content and the conductivity was measured using the obtained molded piece (FIG. 5).

The water content (Water) was obtained by alternately performing electrical resistance measurement and mass measurement (mass), and subtracting the dry weight of the molded piece from the measured mass to obtain the water content during the electrical resistance measurement. The electrical resistance measurement was performed using an electrochemical analyzer ALS 7082E (BAS Co., Ltd.) with an AC impedance method by attaching the molded piece to a glass plate (short side 26 mm, long side 32 mm, thickness 1 mm) having two gold electrodes (short side 4 mm, long side 7.5 mm, spacing 6 mm), which were a positive electrode and a negative electrode obtained by subjecting gold electrodes to sputtering and patterning, so that the molded piece straddled the electrodes. An absolute value of impedance under voltage application conditions of an AC frequency of 1 kHz to 100 kHz, a voltage amplitude of 5 mV and an electric resistance of 82.5 kHz was adopted. The molded piece was infiltrated with McIlvaine buffer (150 mM, pH 7.0), which was used as an electrolyte solution, and all experiments were carried out under conditions of maintaining a temperature of 25° C. and a humidity of 35%. The relationship between the water weight (mg) and the resistance value (Ω) illustrated in FIG. 5C was obtained from the weight change (FIG. 5A) and the resistance change (FIG. 5B) during drying of two samples. Further, FIG. 5D was obtained in consideration of change in the cross-sectional area of the samples due to drying.

It was confirmed that the water content and the conductivity were in a proportional relationship, which demonstrated that the measurement was appropriate (FIG. 5D).

Example 2

Figure 6:
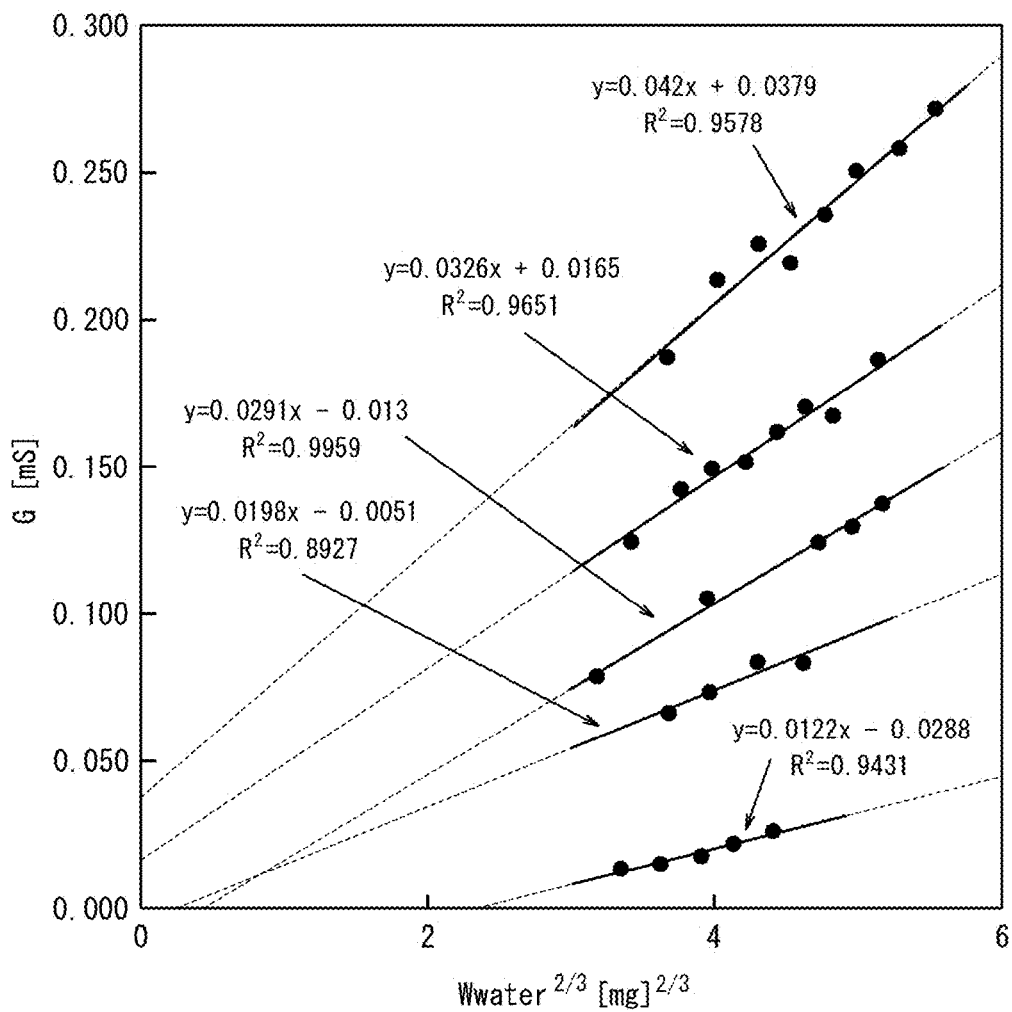
FIG. 6 illustrates the result of Example 2, which is the relationship between the water content and the conductivity of molded pieces having different amounts of methacrylic acid added.

Molded pieces having a thickness of 0.15 mm (corresponding to the thickness of a contact lens) were prepared using the copolymers S1 to S5 described above, and the relationship between the water content and the conductivity was obtained in the same manner as in Example 1 except that the humidity was maintained at 70% using a glove box and a humidifier to slow down the evaporation rate and facilitate the measurement (FIG. 6).

From the result, it is understood that the relationship between the water content and the conductivity (the slope of the line) does not change significantly because of the gel composition, but the value of the conductivity increases as the content of methacrylic acid (monomer having a fixed charge) increases. This indicates that the anti-cation of a carboxy group derived from the methacrylic acid ($Na^+$) is the main conductive carrier.

Example 3

—Water Retention of Hydrogel by Electroosmotic Flow—

Utilizing the fact that the water content can be monitored by the conductivity, the water retention of a hydrogel sheet (thickness 0.15 mm) due to the electroosmotic flow was evaluated.

A hydrogel sheet was sandwiched between two carbon electrodes (for electroosmotic flow generation), which were a positive electrode and a negative electrode arranged on an acrylic plate at an interval of 6 mm, and two gold electrodes (for conductivity measurement) patterned on a glass plate, so that the hydrogel sheet and the electrodes were in contact with each other with a length of 4 mm at the top and bottom, and a middle part with a length of 6 mm was exposed so as not to interfere with natural drying (FIGS. 7A and 7B). One end of 4 mm of the hydrogel sheet was immersed in a McIlvaine buffered aqueous solution (pH 7.0), and the conductivity was measured while maintaining a temperature of 25° C. and a humidity of 35%. The hydrogel sheet was a copolymer S4 in which the adding amount of methacrylic acid was 10 wt %. It was prepared using a copolymer S4 with mechanical strength so that it is easy to handle.

No voltage was applied for the first 25 minutes, and therefore a decrease in conductivity due to natural drying was observed. After that, electric current (about 0.2 mA) was introduced for 30 minutes by applying a voltage of 4 V to the carbon electrodes to pump the buffered aqueous solution upward, so that the conductivity lowered due to natural drying was restored. In this case, the polarity of the applied voltage was negative at the upper part of the hydrogel sheet and positive at the lower part of the hydrogel sheet. After that, when a voltage of 4 V was applied to the carbon electrodes with the polarity reversed and the buffered aqueous solution was discharged from the hydrogel sheet, a decrease in conductivity was observed which indicated that the hydrogel sheet was dried again (FIG. 7B).

These results indicate that the hydrogel sheet can be prevented from drying by energization by applying voltage.

Example 4

—Observation of Electroosmotic Flow—

The occurrence of electroosmotic flow was confirmed by direct observation.

Figure 8:
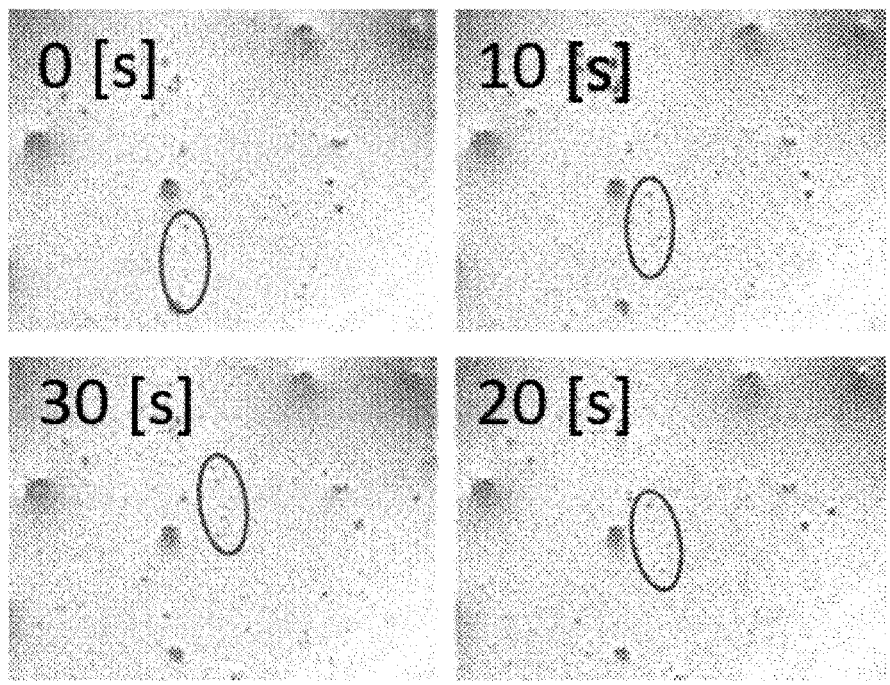
FIG. 8 illustrates the result of confirming the generation of an electroosmotic flow inside a hydrogel sheet by observing the movement of fine particles in Example 4.

Using the same hydrogel sheet (thickness 0.15 mm) and carbon electrodes as the positive and negative electrodes as in Example 3, the upper and lower ends of 4 mm of the hydrogel sheet were in contact with the electrodes, and a length of 6 mm between the electrodes was exposed. The negative electrode side end of 4 mm of the hydrogel sheet was immersed in a McIlvaine buffered aqueous solution (pH 7.0), and electric current (about 0.2 mA) was introduced by applying a voltage of 4 V. A self-made jig was attached to the dry eye observation device (Kowa DR-1α), an upward electroosmotic flow was generated, and the observation results of the exposed portion are illustrated in FIG. 8B. The electroosmotic flow was generated inside the hydrogel sheet, and the movement of the surface water film dragged by the flow inside the hydrogel sheet and the flow caused by the buffer solution overflowing from the inside of the gel were observed.

Example 5

—Water Retention of Contact Lens—
[1] Energization by External Power Source

A contact lens (MA 5 wt %) having the composition of the copolymer S2 was place on the cornea of a porcine eyeball, and a voltage (3V or −3V) was applied using tweezers-shaped electrodes (made of stainless steel) with about ⅓ of the porcine eyeball immersed in a PBS buffered aqueous solution. The contact lens had a thickness of 0.15 mm. Further, the tweezer-shaped electrodes pinched the end portion of the contact lens to fix the position.

Figure 9:
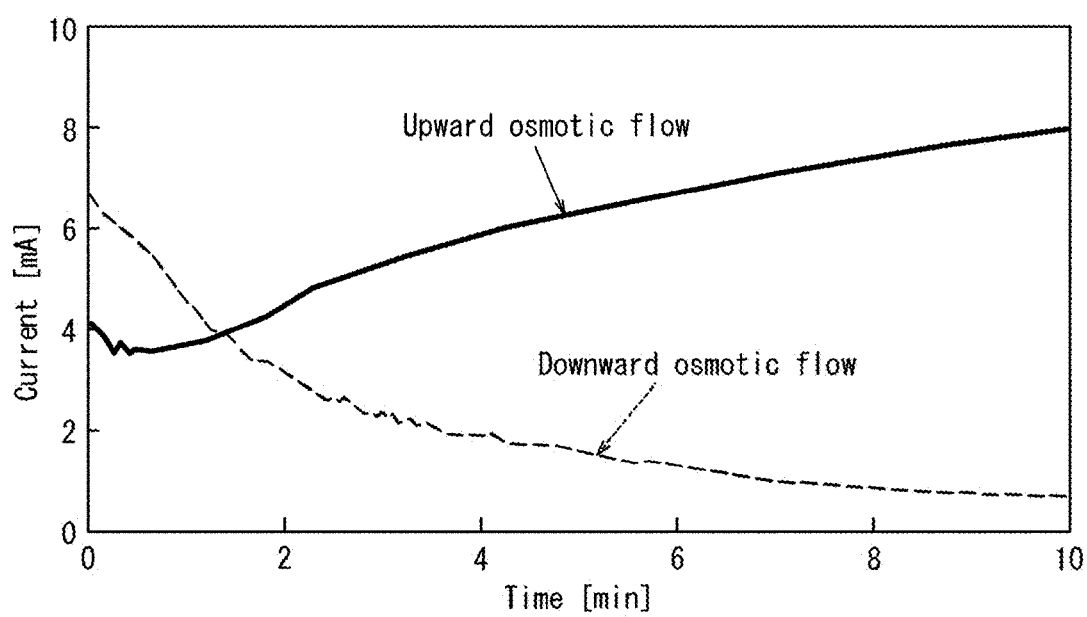
FIG. 9 illustrates the measurement result of conductivity of Example 5 (energization by external power source)

From the results illustrated in FIG. 9, it was confirmed that, in this system where a current reflecting the conductivity (water content) was observed, the water content inside the lens increased due to an upward electroosmotic flow, and the water content decreased due to a downward electroosmotic flow. In a state where an upward electroosmotic flow was applied, the same current value (water content) was being maintained even for 12 hours thereafter. In a case where the contact lens was left for 12 hours without applying a voltage, the contact lens was obviously dried and hardened. Therefore, long-term water absorption and water retention by energization was confirmed. The power here was supplied by being connected to an external power source, but in principle, it is possible to generate an electroosmotic flow by wirelessly supplying power to the electrodes equipped in the contact lens.

[2] Energization by Al/$O_2$ Battery

Figure 10A:
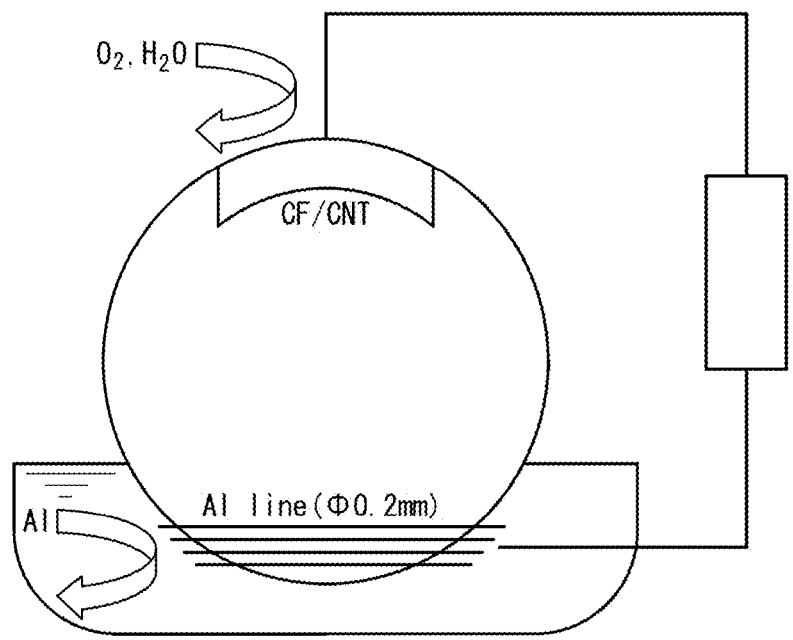
FIG. 10A illustrates an experimental system used for the test of Example 5 (energization by Al/$O_2$ battery)

By installing an Al/$O_2$ battery including an aluminum anode and an $O_2$ cathode of a carbon electrode (CF/CNT) on a contact lens (MA 5 wt %, thickness 0.15 mm) prepared with the copolymer S2, an experiment was conducted in which an electroosmotic flow was generated without using an external power source (FIG. 10A). Because a neutral aqueous solution (0.2 M of NaCl aqueous solution) was used as the solution, the electromotive force was about 0.7 V. The carbon electrode and the aluminum electrode were installed at two ends of the lens, and about ⅓ of the lower end side of the lens including the aluminum electrode was installed so as to be immersed in the neutral aqueous solution. Further, the aluminum electrode and the carbon electrode were electrically connected by a conductive member made of stainless steel that passed through the lens (not illustrated in the drawings). As illustrated in FIG. 10A, the current value was measured by a measuring device connected to the aluminum electrode and the carbon electrode outside the lens.

Figure 10B:
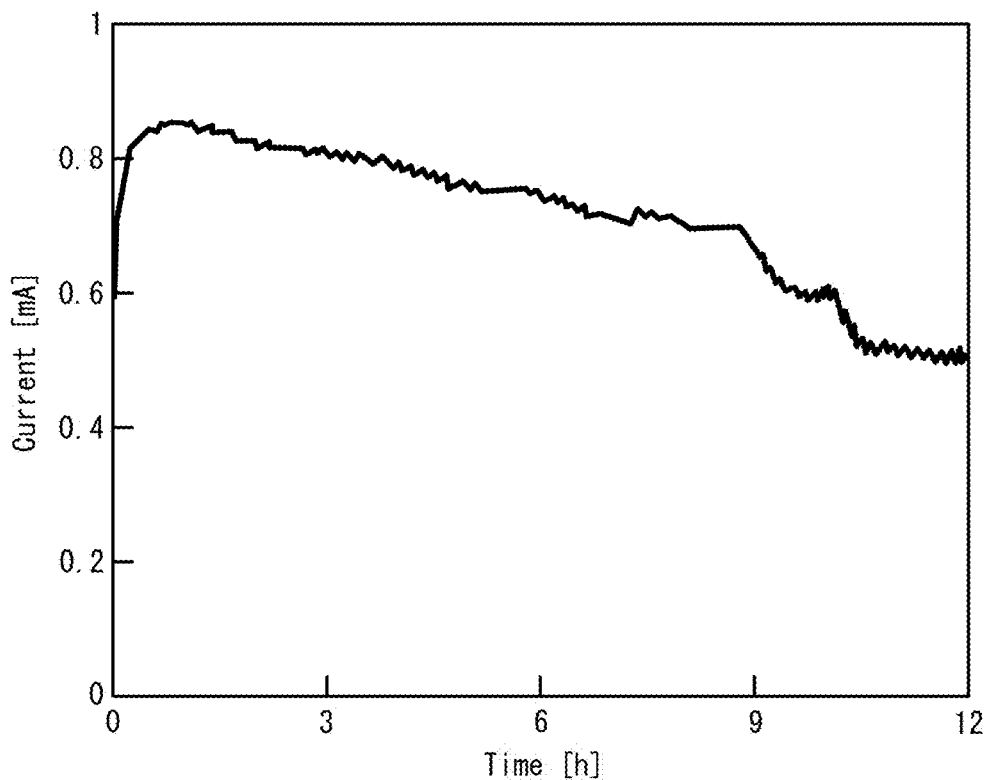
FIG. 10B illustrates the measurement result of conductivity of Example 5 (energization by Al/$O_2$ battery)

From the results illustrated in FIG. 10B, it is understood that the current indicating a wet state continued to flow for even 12 hours because of the effect of an upward electroosmotic flow.

This result indicates that by equipping the contact lens with a battery, it is possible to absorb and retain water without any wiring to the outside.

The anode is not limited to aluminum, and metal-air batteries and any batteries can be used in principle.

[3] Energization by Biological Battery

Figure 11A:
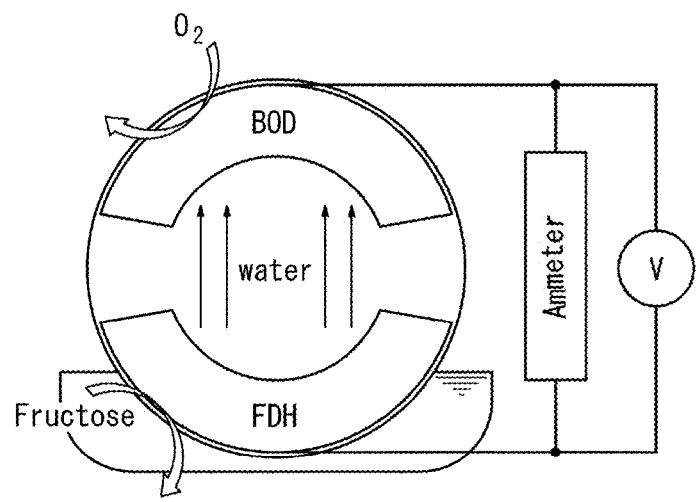
FIG. 11A illustrates an experimental system used for the test of Example 5 (energization by biological battery)

A contact lens (thickness 0.15 mm) prepared with the copolymer S2 was provided with a fructose/$O_2$ biological battery using enzyme electrodes, and the contact lens was placed on a porcine eyeball to verify the water retention by electroosmotic flow. The enzyme electrode of the anode was a carbon fabric (CF) on which fructose dehydrogenase (FDH) had been fixed, and the enzyme electrode of the cathode was a CF on which bilirubin oxidase (BOD) had been fixed. The FDH is an enzyme that catalyzes an electrode reaction that oxidizes fructose, and BOD is an enzyme that catalyzes an electrode reaction that reduces $O_2$. A McIlvaine buffer (150 mM, pH 5.0) containing 200 mM fructose was used as a solution under the contact lens. Further, the FDH electrode and the BOD electrode were electrically connected by a conductive member made of stainless steel. As illustrated in FIG. 11A, the current value was measured by a measuring device connected to the FDH electrode and the BOD electrode.

Figure 11B:
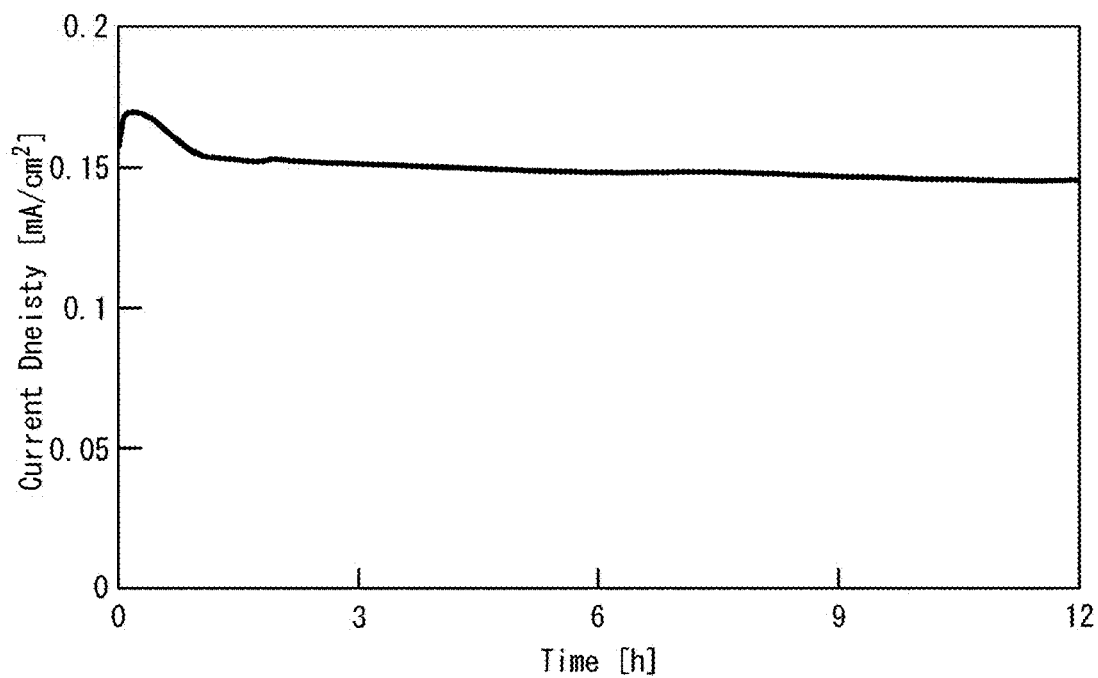
FIG. 11B illustrates the measurement result of conductivity of Example 5 (energization by biological battery).

As illustrated in FIG. 11B, stable energization was confirmed for 12 hours or longer, which suggested that a biological battery using enzyme electrodes could absorb and retain water. The enzyme used for the enzyme electrode may be any oxidoreductase such as glucose oxidase, glucose dehydrogenase, amino acid oxidase, lactate oxidase, and laccase.

INDUSTRIAL APPLICABILITY

According to the method of keeping absorbing or discharging water of a contact lens of the present disclosure, water can be moderately absorbed by a contact lens and/or moderately discharged from a contact lens. Further, the contact lens of the present disclosure has a moderate water absorption capacity and/or water discharge capacity, and by increasing the flow rate of tears on the front surface of the contact lens and on the surface of the eye, the tears can be distributed throughout the surface of the cornea to reduce a feeling of dryness. As a result, it is possible to wear the contact lens for a long period of time. Furthermore, in a case where the water contained in the contact lens contains a drug or the like, the drug or the like contained in the contact lens is released as well as the water absorbed in the lens is released, making it possible to effectively distribute the drug or the like throughout the surface of the eye.

On the other hand, this method is for a wide range of applications. For example, it can be used for a stent that promotes the discharge of aqueous humor to prevent increased intraocular pressure that causes glaucoma, so that the aqueous humor can be actively discharged.

REFERENCE SIGNS LIST

1 contact lens
2 lens portion
31 one electrode
32 the other electrode
4 conductive member
5 outer cover

The invention claimed is:

1. A method of either absorbing or discharging or both absorbing and discharging water of a contact lens, the contact lens including a plurality of electrodes, the contact lens configured to generate an electroosmotic flow both inside and outside the contact lens, wherein the contact lens has a line segment, wherein the line segment is along a surface of the contact lens and passes through a center of the surface of the contact lens and connects one end to another end, only one positive electrode and one negative electrode are on the line segment, and the positive electrode is provided at any position of 0% to 30% from the one end and the negative electrode is provided at any position of 0% to 30% from the other end with respect to a total length of 100% of the line segment.

2. The method of either absorbing or discharging or both absorbing and discharging water of the contact lens according to claim 1, the contact lens including a platform and the plurality of electrodes provided in contact with the platform, and generating an electroosmotic flow inside the platform.

3. The method of either absorbing or discharging or both absorbing and discharging water of the contact lens according to claim 1, wherein the contact lens has a fixed charge.

4. The method of either absorbing or discharging or both absorbing and discharging water of the contact lens according to claim 3, wherein an amount of the fixed charge per unit mass of the contact lens is 1 C/g to 200 C/g.

5. The method of either absorbing or discharging or both absorbing and discharging water of the contact lens according to claim 1, wherein the contact lens comprises a hydrogel material.

6. The method of either absorbing or discharging or both absorbing and discharging water of the contact lens according to claim 5, wherein
the hydrogel material is a polymer material comprising a unit of monomer having the fixed charge, and
a content of the unit of monomer having the fixed charge in the hydrogel material is 0.1 mass % to 20.0 mass %.

7. The method of either absorbing or discharging or both absorbing and discharging water of the contact lens according to claim 6, wherein the unit of monomer having the fixed charge comprises at least one selected from the group consisting of a sulfonic group, a carboxyl group, a phosphate group, and an amino group.

8. The method of either absorbing or discharging or both absorbing and discharging water of the contact lens according to claim 6, wherein the unit of monomer having the fixed charge is a unit of methacrylic acid.

9. The method of either absorbing or discharging or both absorbing and discharging water of the contact lens according to claim 1, wherein the plurality of electrodes is provided at ends of the contact lens.

10. The method of either absorbing or discharging or both absorbing and discharging water of the contact lens according to claim 1, wherein the plurality of electrodes forms a metal/$O_2$ battery.

11. The method of either absorbing or discharging or both absorbing and discharging water of the contact lens according to claim 1, wherein at least one of the plurality of electrodes is an electrode carrying an enzyme that catalyzes an oxidation-reduction reaction.

12. The method of either absorbing or discharging or both absorbing and discharging water of the contact lens according to claim 11, wherein the enzyme comprises at least one selected from the group consisting of bilirubin oxidase and fructose dehydrogenase.

13. The method of either absorbing or discharging or both absorbing and discharging water of the contact lens according to claim 1, wherein an amount of the fixed charge per unit mass of the contact lens is 30 C/g to 100 C/g.

14. A contact lens for either absorbing or discharging or both absorbing and discharging water, comprising a plurality of electrodes and having a line segment, wherein
the line segment is along a surface of the contact lens and passes through a center of the surface of the contact lens and connects one end to another end, only one positive electrode and one negative electrode are on the line segment, and the positive electrode is provided at any position of 0% to 30% from the one end and the negative electrode is provided at any position of 0% to 30% from the other end with respect to a total length of 100% of the line segment, and
generate an electroosmotic flow, both inside and outside the contact lens, between the positive electrode and the negative electrode.

15. The contact lens according to claim 14, which comprises a platform and the plurality of electrodes provided in contact with the platform, and generates an electroosmotic flow between the plurality of electrodes.

16. The contact lens according to claim 14, wherein the contact lens has a fixed charge.

17. The contact lens according to claim 16, wherein an amount of the fixed charge per unit mass of the contact lens is 1 C/g to 200 C/g.

18. The contact lens according to claim 14, wherein the contact lens comprises a hydrogel material.

19. The contact lens according to claim 18, wherein
the hydrogel material is a polymer material containing a unit of monomer having the fixed charge, and
a content of the unit of monomer having the fixed charge in the hydrogel material is 0.1 mass % to 20.0 mass %.

20. The contact lens according to claim 19, wherein the unit of monomer having the fixed charge comprises at least one selected from the group consisting of a sulfonic group, a carboxyl group, a phosphate group and an amino group.

21. The contact lens according to claim 19, wherein the unit of monomer having the fixed charge is a unit of methacrylic acid.

22. The contact lens according to claim 14, wherein the plurality of electrodes is provided at ends of the contact lens.

23. The contact lens according to claim 14, wherein the plurality of electrodes forms a metal/$O_2$ battery.

24. The contact lens according to claim 14, wherein at least one of the plurality of electrodes is an electrode carrying an enzyme that catalyzes an oxidation-reduction reaction.

25. The contact lens according to claim 24, wherein the enzyme comprises at least one selected from the group consisting of bilirubin oxidase and fructose dehydrogenase.

26. The contact lens according to claim 14, wherein an amount of the fixed charge per unit mass of the contact lens is 30 C/g to 100 C/g.

* * * * *